United States Patent
Yamakoshi et al.

(12)

(10) Patent No.: US 10,834,846 B2
(45) Date of Patent: Nov. 10, 2020

(54) ULTRAVIOLET RAY TREATMENT APPARATUS

(71) Applicant: PHOTOSCIENCE JAPAN CORPORATION, Tokyo (JP)

(72) Inventors: Yuji Yamakoshi, Taito-ku (JP); Arata Ishii, Hachioji (JP); Hiroshi Ohara, Kobe (JP)

(73) Assignee: PHOTOSCIENCE JAPAN CORPORATION, Tokyo (JP)

( * ) Notice: Subject to any disclaimer, the term of this patent is extended or adjusted under 35 U.S.C. 154(b) by 0 days.

(21) Appl. No.: 16/546,690

(22) Filed: Aug. 21, 2019

(65) Prior Publication Data

US 2020/0093030 A1    Mar. 19, 2020

(30) Foreign Application Priority Data

Sep. 14, 2018   (JP) .................. 2018-172906

(51) Int. Cl.
| | |
|---|---|
| *H05K 7/00* | (2006.01) |
| *H05K 7/20* | (2006.01) |
| *C02F 1/32* | (2006.01) |
| *A61L 2/10* | (2006.01) |

(52) U.S. Cl.
CPC .......... *H05K 7/20172* (2013.01); *A61L 2/10* (2013.01); *C02F 1/325* (2013.01); *H05K 7/20209* (2013.01); *A61L 2202/11* (2013.01); *A61L 2202/14* (2013.01); *C02F 2201/326* (2013.01); *C02F 2303/04* (2013.01)

(58) Field of Classification Search
CPC ...................... H05K 7/20172; H05K 7/20209; C02F 1/325; C02F 2303/04; C02F 2201/326; A61L 2/10; A61L 2202/14; A61L 2202/11

USPC ................... 250/453.11–455.11, 504 R
See application file for complete search history.

(56) References Cited

U.S. PATENT DOCUMENTS

| | | | | |
|---|---|---|---|---|
| 5,372,781 A | * | 12/1994 | Hallett | ............ A61L 2/10 422/186 |
| 5,505,912 A | * | 4/1996 | Hallett | ............ A61L 2/10 422/186.3 |
| 5,547,635 A | * | 8/1996 | Duthie, Jr. | ............ A61L 2/10 250/455.11 |

(Continued)

FOREIGN PATENT DOCUMENTS

WO        2016143829 A1    9/2016

*Primary Examiner* — Michael Maskell
(74) *Attorney, Agent, or Firm* — Rossi, Kimms & McDowell LLP

(57) ABSTRACT

A disclosed apparatus includes: a vessel accommodating an object to be treated; an ultraviolet ray lamp that emits ultraviolet rays to the object to be treated; a control unit accommodating circuit equipment that controls energization of the ultraviolet ray lamp; and two (i.e., first and second) fans disposed in series with each other in an exhaust opening, formed in a casing of the control unit, for cooling the circuit equipment within the control unit. While the apparatus is in operation, the first fan is normally kept in a driven state and an air flow exhausted by the first fan passes through the second fan while idling the second fan. The apparatus further includes an abnormality detector that detects an abnormality of the first fan, such that the second fan is activated in response to the abnormality of the first fan being detected by the abnormality detector.

7 Claims, 1 Drawing Sheet

(56) References Cited

U.S. PATENT DOCUMENTS 6,458,331 B1 * 10/2002 Roberts .................. A61L 2/10
                                                       422/186.3
10,040,700 B2    8/2018 Akiyama et al.

* cited by examiner

ULTRAVIOLET RAY TREATMENT APPARATUS

PRIORITY

This application is based on, and claims priority to, Japanese Patent Application No. 2018-172906 filed on 14 Sep. 2018. The disclosure of the priority application, in its entirety, including the drawings, claims, and the specification thereof, are incorporated herein by reference.

BACKGROUND

The present invention relates generally to ultraviolet ray treatment apparatus and more particularly to a structure for cooling control equipment provided in an ultraviolet ray treatment apparatus.

In factories that manufacture semiconductors or FPDs (Flat Panel Displays), ultrapure water is used in product manufacturing steps. Water quality items of the ultrapure water include a viable bacteria count and a TOC (Total Organic Carbon) concentration. Ultraviolet ray sterilization apparatus are used as one form of equipment for inactivating microorganisms, and low-pressure UV oxidation apparatus are used as one form of equipment for reducing the TOC concentration. In these apparatus, one or more low-pressure mercury lamps are snugly provided in a circular reaction vessel so as to emit ultraviolet rays of 254 or 185 nm light. The low-pressure mercury lamps are each inserted in a respective (or dedicated) lamp protecting tube formed of quartz in such a manner that the lamp does not directly contact water to be treated (namely, to-be-treated water) within the reaction vessel. The to-be-treated water is pressure-fed between the outside surface of the lamp protecting tube and the inside surface of the reaction vessel while being exposed to, or irradiated with, the ultraviolet rays. Microorganisms present in the treated water are inactivated by being exposed to, or irradiated with, the ultraviolet rays of 254 nm light. Such inactivation is commonly referred to also as sterilization. Further, OH radicals are produced from the treated water exposed to the ultraviolet rays of 185 nm light, and the produced OH radicals function as an oxidizing agent to oxidatively decompose the TOC. At the same time, organic substances are decomposed directly by the 185 nm light and 254 nm light emitted from the low-pressure mercury lamps. Similar reactions can be caused by use of a medium-pressure mercury lamp, a high-pressure mercury lamp, an excimer lamp, or the like other than the low-pressure mercury lamp, as long as the lamp used is a light source (ultraviolet ray lamp) that emits light of a wavelength of 300 nm or less. Quarts, sapphire, fluorine resin, or the like is used as a material of the lamp protecting tube. International Patent Application Publication WO 2016/143829 discloses an example of such an ultraviolet ray treatment apparatus.

Generally, because the ultraviolet ray treatment apparatus includes a control unit for controlling energization of, or power supply to, the lamp and a ballast included in the control unit generates a great amount of heat, it is essential to provide a cooling device in the form of a cooling fan. In such a case, it is desirable, for fail-safe purposes, that a dual-fan structure be provided in such a manner as to ensure appropriate cooling performance even when one of the two fans has failed. However, it has been known that inconveniences would occur if the two fans are disposed in an exhaust opening in parallel with each other. For example, when one of the two fans disposed in the exhaust opening in parallel with each other has stopped operating due to a failure, external air enters in an opposite direction through the exhaust opening and through the faulty fan due to suction power of the other fan appropriately operating, which would reduce the amount of air to be taken in through an air intake opening and thereby undesirably lower the cooling performance within the control unit.

SUMMARY

In view of the foregoing prior art problems, it is one of the objects of the present invention to provide an ultraviolet ray treatment apparatus which includes a dual-fan structure having two fans disposed in an improved manner so as to perform an appropriate fail-safe function without incurring lowering of cooling performance.

In order to accomplish the aforementioned and other objects, the inventive ultraviolet ray treatment apparatus includes: a vessel accommodating an object to be treated; an ultraviolet ray lamp that emits ultraviolet rays to the object to be treated; a control unit accommodating circuit equipment that controls energization of the ultraviolet ray lamp; and two fans disposed in series with each other in an exhaust opening, formed in a casing of the control unit, for cooling the circuit equipment within the control unit.

According to the inventive ultraviolet ray treatment apparatus, the two fans (cooling fans) are disposed in series with each other in the exhaust opening. Thus, even when one of the two cooling fans has failed, a flowing direction of an exhaust flow in the exhaust opening does not change, so that there occurs no unwanted phenomenon where external air enters in an opposite direction through the exhaust opening. In this way, it is possible to minimize the lowering of the cooling performance within the control unit.

In an embodiment, the ultraviolet ray treatment apparatus may be constructed in such a manner that while the ultraviolet ray treatment apparatus is in operation, a first one of the two fans is normally (namely, under normal conditions) kept in a driven state and an air flow exhausted by the first fan passes through a second one of the two fans while idling the second fan. The inventive ultraviolet ray treatment apparatus may further include an abnormality detector that detects an abnormality of the first fan such that the second fan is activated in response to the abnormality of the first fan being detected by the abnormality detector.

BRIEF DESCRIPTION OF THE DRAWINGS

Certain preferred embodiments of the present invention will hereinafter be described in detail, by way of example only, with reference to the accompanying drawings, in which.

DETAILED DESCRIPTION

Figure 1:
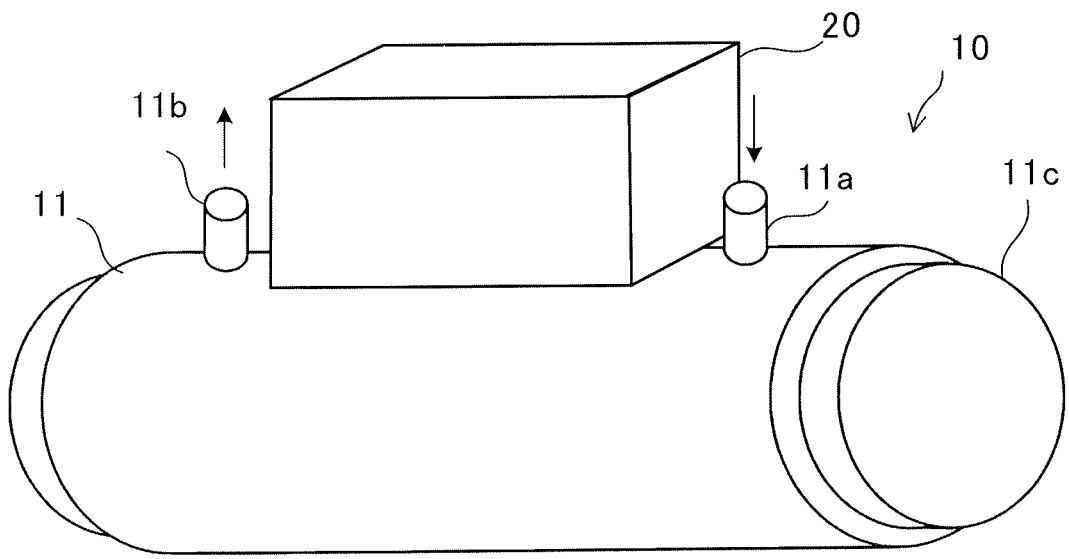
FIG. 1 is a perspective view schematically illustrating an outer appearance of an embodiment of the inventive ultraviolet ray treatment apparatus.

FIG. 1 is a perspective schematically illustrating an outer appearance of an embodiment of the inventive ultraviolet ray treatment apparatus 10 which is constructed, as an example, to perform ultraviolet ray treatment of liquid. In the illustrated example, the embodiment of the inventive ultraviolet ray treatment apparatus 10 is constructed to perform ultrapure water treatment as set forth above in the introductory part of this specification. A vessel 11 is a closed-type circular vessel having an intake port 11*a* for taking in liquid as an object to be treated by the ultraviolet ray treatment apparatus 10 and an exhaust port 11*b* for discharging liquid having been treated by the ultraviolet ray treatment apparatus 10. At least one ultraviolet ray lamp 12 (FIG. 3) is installed within the vessel 11 to emit ultraviolet rays to the liquid (object to be treated) flowing within the vessel 11. When the lamp 12 is to be replaced, a cap 11*c* provided at one end of the vessel 11 is opened so that the lamp 12 can be accessed and detached and then a new lamp 12 or another lamp 12 can be attached.

Figure 2:
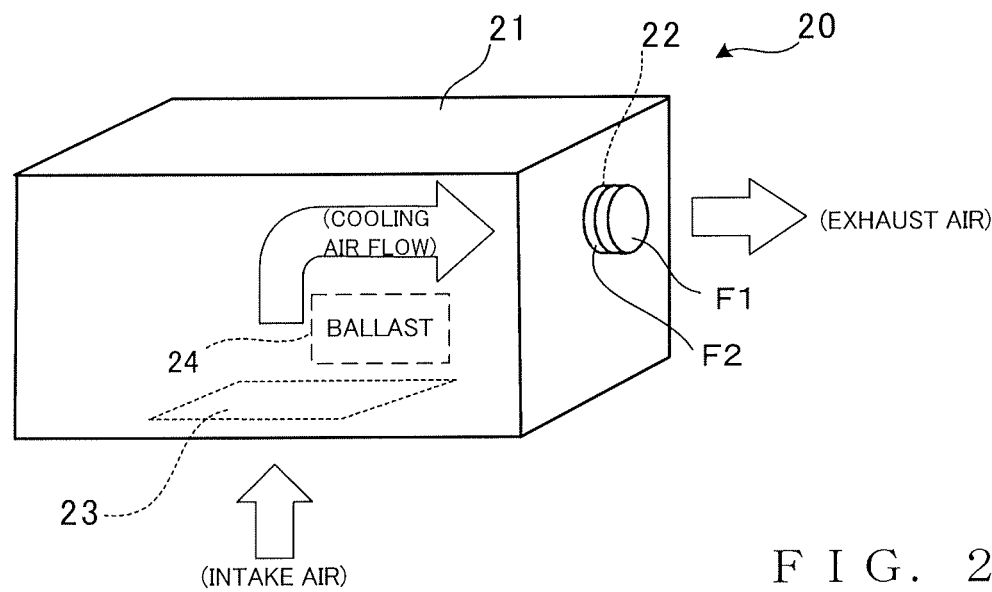
FIG. 2 is a schematic view illustrating a cooling structure of a control unit of FIG. 1.

A control unit 20 is disposed on a suitable outside portion (upper outside portion in the illustrated example) of the vessel 11. Various pieces of circuit equipment, such as a ballast 24, for controlling energization of the ultraviolet ray lamp 12 is accommodated in a casing 21 of the control unit 20. In order to cool the ballast 24 and the like that generate heat within the control unit 20, an exhaust opening 22 is formed in the casing 21 of the control unit 20, and two fans F1 and F2 are disposed in series with each other in the exhaust opening 22, as illustrated in FIG. 2. Further, an air intake opening 23 is formed in a suitable portion of the casing 21 of the control unit 20. In response to the fans F1 and F2 disposed in the exhaust opening 22 being driven, external air is sucked, through the air intake opening 23, into the casing 21, a cool air flow cools the circuit equipment, such as the ballast 24, accommodated in the casing 21 while passing within the casing 21, and then the air flow having become warm within the casing 21 is discharged through the exhaust opening 22, as schematically depicted by arrows in the figure. Needless to say, such an air cooling (head exchange) mechanism itself is conventionally known. The air intake opening 23 may be formed in a plurality of portions, rather than just one portion, of the casing 21, such that the circuit equipment, such as the ballast 24, can be cooled more efficiently.

The embodiment of the inventive ultraviolet ray treatment apparatus 10 is characterized in that the two fans 22 are disposed in series with each other in the exhaust opening 22. As an example, while the ultraviolet ray treatment apparatus 10 is in operation, the first fan (for example, fan F1) of the two fans F1 and F2 is normally (namely, under normal conditions) kept in a driven state (namely, kept powered on) while the second fan (for example, fan F2) is normally kept in a non-driven state (kept powered off). In this case, the air flow discharged through the exhaust opening 22 by the driving of the first fan F1 passes through the second fan F2 while idling the fan F2 kept in the non-driven state (causing the fan F2 to co-rotate with the first fan F1 at a low number of rotations). Let it be assumed here that the normally-driven first fan F1 has exhausting power necessary and sufficient to cool the circuit equipment, such as the ballast 24, accommodated within the casing 21.

As will be described in detail later, once the normally-driven first fan F1 fails or stops operating appropriately, the second fan F2 is activated so that the air flow is discharged through the exhaust opening 22 by the exhausting power of the second fan F2, thereby ensuring a capability to cool the circuit equipment, such as the ballast 24, within the casing 21. Therefore, it is preferable that the exhausting power of the second fan F2 be equal to that of the first fan F1. However, the respective exhausting power of the first and second fans F1 and F2 may be different from each other as necessary rather than equal to each other. Namely, if the operating time period of the second fan F2, operating in place of the faulty first fan F1, is considered as a temporary relief period over which the second fan F2 should operate until the faulty first fan F1 is replaced with a new one or another one, the exhausting power of the second fan F2 may be somewhat lower than that of the first fan F1.

According to the present embodiment, as set forth above, the two fans F1 and F2 are disposed in series with each other in the exhaust opening 22. Therefore, even when one of the two fans has failed, a flowing direction of an exhaust flow in the exhaust opening 22 does not change and thus there occurs no unwanted phenomenon where external air enters in the opposite direction through the exhaust opening 22, as along as the other fan is operating appropriately. Therefore, in the case where the two fans F1 and F2 are disposed in series with each other, it is possible to minimize the lowering of the cooling performance within the control unit 20 when one of the fans has failed, as compared to the case where the two fans F1 and F2 are disposed in parallel with each other.

Figure 3:
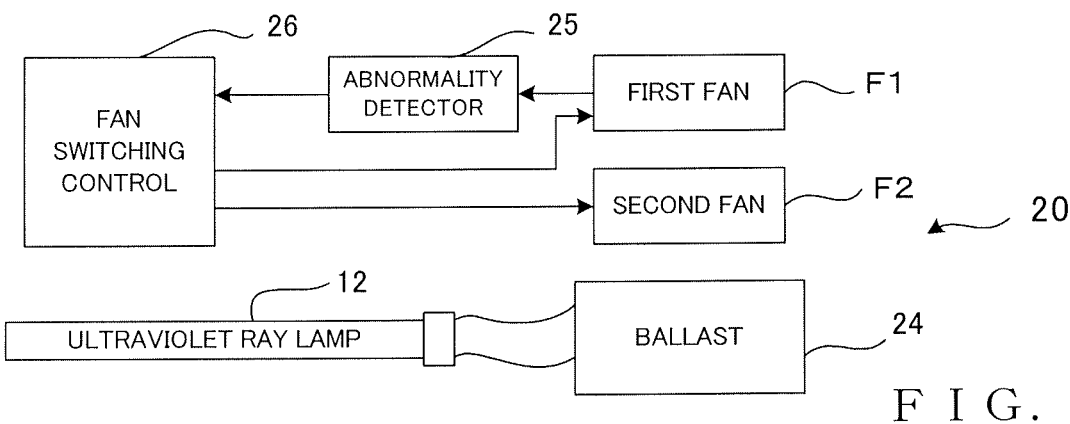
FIG. 3 is a block diagram explanatory of cooling control performed via the control unit.

FIG. 3 is a block diagram explanatory of cooling control performed via the control unit 20. An abnormality detector 25 is provided for the first fan F1, and the abnormality detector 25 detects that the first fan F1 has an abnormality when the number of rotations of the first fan F1 being energized has decreased below a predetermined threshold value. While the ultraviolet ray treatment apparatus 10 is in operation, a fan switching control section 26 controls the energization of the individual fans F1 and F2 in such a manner that the first fan F1 is normally kept in the driven state (kept powered on) while the second fan F2 is normally kept in the non-driven state (kept powered off). Once any abnormality of the first fan F1 is detected by the abnormality detector 25, the abnormality detector 25 generates an abnormality detection signal, and the fan switching control section 26 performs automatic control, on the basis of the abnormality detection signal, such that the first fan F1 is powered off and the second fan F2 is switched to the driven state (powered on). Namely, once the normally-driven first fan F1 fails, the second fan F2 is automatically activated in such a manner that the air flow is discharged through the exhaust opening 22 by the exhausting power of the second fan F2. In this way, the present embodiment can ensure an appropriate cooling capability to cool the circuit equipment, such as the ballast 24, within the casing 21 and thereby achieves an appropriate fail-safe function.

Note that an abnormality detector, such as the aforementioned abnormality detector for the first fan F1, does not necessarily have to be provided for the second fan F2. Namely, if an abnormality detector in the form of a simple number-of-rotation decrease detector is provided for the second fan F2, a phenomenon where, when the powered-off second fan F2 is caused to co-rotate at a low number of rotations, such a low number of rotations of the powered-off second fan F2 might be erroneously detected as a number-of-rotation decrease abnormality, and therefore, it is more convenient that such an abnormality detector be not provided for the second fan F2. If such an abnormality detector is not provided for the second fan F2, however, there occurs a problem that no abnormality of the second fan F2 can be detected. Therefore, when the faulty first fan F1 is to be replaced with a new one or another one, the second fan F2 having no abnormality may also be replaced with a new one or another one.

Although only one exhaust opening 22 is provided in the casing 21 of the control unit 20 in the illustrated example, the embodiments of the present invention are not so limited, and two or more such exhaust openings 22 may be provided in the casing 21. In such a case, two fans F1 and F2 may be disposed in series with each other in each of the exhaust openings 22. However, the embodiments of the present invention are not so limited, and two fans F1 and F2 may be disposed in series with each other in at least one of the exhaust openings 22.

As another modification, three or more fans F1, F2, . . . may be provided in series with one another in one exhaust opening 22. In such a case, power-on and power-off control of the individual fans may be executed in such a manner that while the ultraviolet ray treatment apparatus 10 is in operation, one or two or more of the fans (for example, the first fan F1) are normally kept in the driven state (kept powered on) while the other fan or fans (for example, the second fan F2) are normally kept in the non-driven state (kept powered off).

In the inventive ultraviolet ray treatment apparatus, the vessel accommodating the object to be treated is not limited to the aforementioned closed-type vessel 11 and may be an open-type vessel having an upper end portion communicating with an external space. Further, the object to be treated is not limited to water or other liquid alone and may be a solid substance. In the case where the object to be treated is a solid substance, the vessel accommodating the object to be treated is a treating vessel or chamber that provides a treating space for exposing the to-be-treated solid substance to the ultraviolet rays irradiated from the ultraviolet ray lamp 12.

What is claimed is:

1. An ultraviolet ray treatment apparatus comprising:
   a vessel configured to accommodate an object to be treated;
   an ultraviolet ray lamp that emits ultraviolet rays to the object to be treated;
   a control unit including circuit equipment that controls energization of the ultraviolet ray lamp; and
   a first fan and a second fan disposed in series with each other in an exhaust opening, formed in a casing of the control unit, and configured to cool the circuit equipment within the control unit,
   wherein in a case where the ultraviolet ray treatment apparatus is in normal operation, the first fan is kept in a driven state and an air flow exhausted by the first fan passes through the second fan while the second fan is kept in an idle state.

2. The ultraviolet ray treatment apparatus as claimed in claim 1, further comprising an abnormality detector that detects an abnormality of the first fan, and
   wherein the second fan is configured to be activated in response to the abnormality of the first fan being detected by the abnormality detector.

3. The ultraviolet ray treatment apparatus as claimed in claim 2, wherein the abnormality detector is of a type that detects the abnormality of the first fan in a case where a number of rotations of the first fan being energized has decreased below a predetermined threshold value, and no abnormality detector of the type is provided for the second fan.

4. The ultraviolet ray treatment apparatus as claimed in claim 3, wherein when the first fan detected by the abnormality detector as having the abnormality is to be replaced, the second fan is replaced together with the first fan.

5. The ultraviolet ray treatment apparatus as claimed in claim 1, wherein one or more air intake openings are formed in the casing of the control unit.

6. The ultraviolet ray treatment apparatus as claimed in claim 1, wherein two or more exhaust openings are formed in the casing of the control unit, and at least two fans are disposed in series with each other in each of the two or more exhaust openings.

7. The ultraviolet ray treatment apparatus as claimed in claim 1, wherein the object to be treated is a liquid.

* * * * *